(12) United States Patent
Robinson et al.

(10) Patent No.: US 6,622,032 B1
(45) Date of Patent: Sep. 16, 2003

(54) METHOD FOR NON-INVASIVE BLOOD ANALYTE MEASUREMENT WITH IMPROVED OPTICAL INTERFACE

(75) Inventors: Mark Ries Robinson, Albuquerque, NM (US); Robert G. Messerschmidt, Albuquerque, NM (US)

(73) Assignee: InLight Solutions, Inc., Albuquerque, NM (US)

( * ) Notice: Subject to any disclaimer, the term of this patent is extended or adjusted under 35 U.S.C. 154(b) by 457 days.

(21) Appl. No.: 09/672,373

(22) Filed: Sep. 28, 2000

Related U.S. Application Data

(63) Continuation of application No. 09/174,812, filed on Oct. 19, 1998, now Pat. No. 6,152,876, which is a continuation-in-part of application No. 08/844,501, filed on Apr. 18, 1997, now Pat. No. 5,823,951, which is a continuation of application No. 08/512,940, filed on Aug. 9, 1995, now Pat. No. 5,655,530.

(51) Int. Cl.⁷ .................................................. A61B 5/50
(52) U.S. Cl. ....................................... 600/310; 600/322
(58) Field of Search ................................. 600/310, 322, 600/323, 473; 514/744, 937, 941; 252/408.1, 582

(56) References Cited

U.S. PATENT DOCUMENTS

| | | | |
|---|---|---|---|
| 3,508,304 A | 4/1970 | Hopkins et al. | 356/103 |
| 4,169,807 A | 10/1979 | Zuber | 252/171 |
| 4,461,718 A * | 7/1984 | Kaye et al. | 252/408.1 |
| 4,655,225 A | 4/1987 | Dahne et al. | |
| 4,661,706 A | 4/1987 | Messerschmidt et al. | 250/341 |
| 4,853,542 A | 8/1989 | Milosevic et al. | 250/353 |
| 4,882,492 A | 11/1989 | Schlager | 250/346 |
| 4,975,581 A | 12/1990 | Robinson et al. | 250/339 |
| 5,015,100 A | 5/1991 | Doyle | 356/445 |
| 5,019,715 A | 5/1991 | Sting et al. | 250/571 |
| 5,028,787 A | 7/1991 | Rosenthal et al. | 250/341 |
| 5,070,874 A | 12/1991 | Barnes et al. | |
| 5,158,082 A | 10/1992 | Jones | |
| 5,222,496 A | 6/1993 | Clarke et al. | |
| 5,237,178 A | 8/1993 | Rosenthal et al. | 250/341 |
| 5,299,570 A | 4/1994 | Hatschek | |
| 5,321,265 A | 6/1994 | Block | 250/343 |
| 5,348,003 A | 9/1994 | Caro | |
| 5,355,880 A | 10/1994 | Thomas et al. | |
| 5,372,135 A | 12/1994 | Mendelson et al. | |
| 5,379,764 A | 1/1995 | Barnes et al. | |
| 5,402,778 A | 4/1995 | Chance | |

(List continued on next page.)

FOREIGN PATENT DOCUMENTS

| | | |
|---|---|---|
| EP | 0 280 418 A1 | 8/1988 |
| WO | WO 92/17765 | 10/1992 |
| WO | WO 9307801 | 4/1993 |

OTHER PUBLICATIONS

Marbach, "Measurement Techniques for IR Spectroscopic Blood Glucose Determination", 1993.

*Primary Examiner*—Eric F Winakur
(74) *Attorney, Agent, or Firm*—Crompton, Seager, & Tufte, LLC; David Crompton

(57) ABSTRACT

A method for non-invasively measuring the concentration of an analyte, particularly blood analyte in blood. The method utilizes spectrographic techniques in conjunction with an improved optical interface between a sensor probe and a skin surface or tissue surface of the body containing the blood to be analyzed. An index-matching medium is disclosed to improve the interface between the sensor probe and skin surface during spectrographic analysis. In a preferred embodiment, the blood analyte concentration in blood is quantified utilizing a partial squares analysis relative to a model incorporating analysis of plural known blood samples.

9 Claims, 2 Drawing Sheets

U.S. PATENT DOCUMENTS

| | | |
|---|---|---|
| 5,435,309 A | 7/1995 | Thomas et al. |
| 5,452,723 A | 9/1995 | Wu et al. |
| 5,495,032 A | 2/1996 | Robinson et al. |
| 5,505,726 A | 4/1996 | Meserol .................. 606/9 |
| 5,527,386 A * | 6/1996 | Statz ..................... 252/586 |
| 5,533,509 A | 7/1996 | Koashi et al. |
| 5,596,992 A | 1/1997 | Haaland et al. |
| 5,630,413 A | 5/1997 | Thomas et al. |
| 5,636,633 A | 6/1997 | Messerschmidt et al. |
| 5,655,530 A | 8/1997 | Messerschmidt et al. |
| 5,792,050 A | 8/1998 | Alam et al. .................. 600/310 |
| 5,823,951 A | 10/1998 | Messerschmidt et al. ... 600/322 |
| 5,830,132 A | 11/1998 | Robinson .................. 600/311 |
| 5,857,462 A | 1/1999 | Thomas et al. |
| 5,935,062 A | 8/1999 | Messerschmidt ............ 600/322 |
| 6,152,876 A | 11/2000 | Robinson et al. ........... 600/322 |
| 6,157,041 A | 12/2000 | Thomas et al. ............. 250/573 |

* cited by examiner

METHOD FOR NON-INVASIVE BLOOD ANALYTE MEASUREMENT WITH IMPROVED OPTICAL INTERFACE

CROSS REFERENCES TO CO-PENDING APPLICATIONS

This Application is a continuation of application Ser. No. 09/174,812, filed Oct. 19, 1998, now U.S. Pat. No. 6,152, 876, which is a Continuation-in-part of U.S. Patent Application Ser. No. 08/844,501, filed Apr. 18, 1997, entitled "Method for Non-Invasive Blood Analyte Measurement with Improved Optical Interface", now U.S. Pat. No. 5,823, 951, issued Oct. 20, 1998, to the same assignee as the present application which is a continuation of Ser. No. 08/512,940 filed Aug. 9, 1995 now U.S. Pat. No. 5,655,530.

TECHNICAL FIELD

The present invention relates generally to a non-invasive method for measuring a blood analyte, particularly glucose, utilizing spectroscopic methods. More particularly, the method incorporates an improved input optical interface for irradiating biological tissue with infrared energy having at least several wavelengths and an improved output optical interface for receiving non-absorbed infrared energy as a measure of differential absorption by the biological sample to determine an analyte concentration. An index-matching medium is disclosed as a key element of the improved optical interface.

BACKGROUND OF THE INVENTION

The need and demand for an accurate, non-invasive method for determining blood glucose level in patients is well documented. Barnes et al. (U.S. Pat. No. 5,379,764) disclose the necessity for diabetics to frequently monitor glucose levels in their blood. It is further recognized that the more frequent the analysis, the less likely there will be large swings in glucose levels. These large swings are associated with the symptoms and complications of the disease, whose long term effects can include heart disease, arteriosclerosis, blindness, stroke, hypertension, kidney failure, and premature death. As described below, several systems have been proposed for the non-invasive measurement of glucose in blood. However, despite these efforts a lancet cut into the finger is still necessary for all presently commercially available forms of home glucose monitoring. This is believed so compromising to the diabetic patient that the most effective use of any form of diabetic management is rarely achieved.

The various proposed non-invasive methods for determining blood glucose level, discussed individually below, generally utilize quantitative infrared spectroscopy as a theoretical basis for analysis. Infrared spectroscopy measures the electromagnetic radiation (0.7–25 $\mu$m) a substance absorbs at various wavelengths. Molecules do not maintain fixed positions with respect to each other, but vibrate back and forth about an average distance. Absorption of light at the appropriate energy causes the molecules to become excited to a higher vibration level. The excitation of the molecules to an excited state occurs only at certain discrete energy levels, which are characteristic for that particular molecule. The most primary vibrational states occur in the mid-infrared frequency region (i.e., 2.5–25 $\mu$m). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the blood which also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood, and that the resulting spectral data may exhibit a non-linear response due to both the properties of the substance being examined and/or inherent non-linearities in optical instrumentation.

A further common element to non-invasive glucose measuring techniques is the necessity for an optical interface between the body portion at the point of measurement and the sensor element of the analytical instrument. Generally, the sensor element must include an input element or means for irradiating the sample point with infrared energy. The sensor element must further include an output element or means for measuring transmitted or reflected energy at various wave lengths resulting from irradiation through the input element.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

Several of the embodiments disclosed by Robinson et al. are non-invasive and incorporate an optical interface having a sensor element. As depicted in FIGS. 5 and 6 of Robinson et al., the optical interface includes first, an input element and second, an output element. The input element is an infrared light source or near infrared light source. The input element interface with the sample or body portion containing blood to be tested includes transmitting the light energy or propagating the light energy to the surface of the skin via the air. The output element includes a detector which receives the transmitted or reflected light energy. The output interface with the sample also includes propagating the transmitted or reflected light through the air from the skin.

Barnes et al. (U.S. Pat. No. 5,379,764) disclose a spectrographic method for analyzing glucose concentration, wherein near infrared radiation is projected on a portion of the body, the radiation including a plurality of wavelengths, followed by sensing the resulting radiation emitted from the portion of the body as affected by the absorption of the body. The method disclosed includes pretreating the resulting data to minimize influences of offset and drift to obtain an expression of the magnitude of the sensed radiation as modified.

The sensor element disclosed by Barnes et al. includes a dual conductor fiber optic probe which is placed in contact or near contact with the skin of the body. The first conductor of the dual conductor fiber optic probe acts as an input element which transmits the near infrared radiation to the skin surface while in contact therewith. The second conductor fiber of the dual conductor probe acts as an output element which transmits the reflected energy or non-absorbed energy back to a spectrum analyzer. The optical interface between the sensor element and the skin is achieved by simply contacting the skin surface with the probe, and can include transmitting the light energy through air to the skin and through air back to the probe depending upon the degree of contact between the probe and skin. Irregularities in the skin surface and at the point of measurement will affect the degree of contact.

Dähine et al. (U.S. Pat. No. 4,655,225) disclose the employment of near infrared spectroscopy for non-invasively transmitting optical energy in the near infrared spectrum through a finger or earlobe of a subject. Also discussed is the use of near infrared energy diffusely reflected from deep within the tissues. Responses are derived at two different wavelengths to quantify glucose in the subject. One of the wavelengths is used to determine background absorption, while the other wavelength is used to determine glucose absorption.

The optical interface disclosed by Dähne et al. includes a sensor element having an input element which incorporates a directive light means which is transmitted through the air to the skin surface. The light energy which is transmitted or reflected from the body tissue as a measure of absorption is received by an output element. The interface for the output element includes transmitting the reflected or transmitted light energy through air to the detector elements.

Caro (U.S. Pat. No. 5,348,003) discloses the use of temporally-modulated electromagnetic energy at multiple wavelengths as the irradiating light energy. The derived wavelength dependence of the optical absorption per unit path length is compared with a calibration model to derive concentrations of an analyte in the medium.

The optical interface disclosed by Caro includes a sensor element having an input element, wherein the light energy is transmitted through a focusing means onto the skin surface. The focusing means may be near or in contact with the skin surface. The sensor element also includes an output element which includes optical collection means which may be in contact with the skin surface or near the skin surface to receive light energy which is transmitted through the tissue. Again, a portion of the light energy is propagated through air to the skin surface and back to the output element due to non-contact with the sensor and irregularities in the skin surface.

Problems with the optical interface between the tissue and the instrument have been recognized. In particular, optical interface problems associated with coupling light into and back out of the tissue were recognized by Ralf Marbach as published in a thesis entitled "Meßverfahren zur IR-spektroskopishen Blutglucose Bestimmung" (English translation "Measurement Techniques for IR Spectroscopic Blood Glucose Determination"), published in 1993.

Marbach states that the requirements of the optical accessory for measurement of the diffuse reflection of the lip are:
1) High optical "throughput" for the purpose of optimizing the S/N ratio of the spectra,
2) Suppression of the insensitivity to Fresnel or specular reflection on the skin surface area.

The measurement accessory proposed by Marbach attempts to meet both requirements through the use of a hemispherical immersion lens. The lens is made out of a material which closely matches the refractive index of tissue, calcium fluoride. As stated by Marbach, the important advantages of the immersion lens for transcutaneous diffuse reflection measurements are the nearly complete matching of the refraction indices of $CaF_2$ and skin and the successful suppression of the Fresnel reflection.

Calcium fluoride, however is not an ideal index match to tissue, having an index of 1.42, relative to that of tissue, at approximately 1.38. Thus, an index mismatch occurs at the lens to tissue interface assuming complete contact between the lens and tissue. The optical efficiency of the sampling accessory is further compromised by the fact that the lens and the tissue will not make perfect optical contact due to roughness of the tissue. The result is a significant refractive index mismatch where the light is forced to travel from the lens (N=1.42) to air (N=1.0) to tissue (N=1.38). Thus, the inherent roughness of tissue results in small air gaps between the lens and the tissue, which decrease the optical throughput of the system, and subsequently compromise the performance of the measurement accessory.

The magnitude of the problem associated with refractive index mismatch is a complicated question. First, a fraction of light, which would otherwise be available for spectroscopic analysis of blood analytes, gets reflected at the mismatch boundary and returns to the input or collection optical system without interrogating the sample. The effect is $$R = \frac{(N' - N)^2}{(N' + N)^2}$$

governed by the Fresnel Equation:
For normally incident, randomly polarized light, where N and N' are the refractive indices of the two media. Solving for the air/CaF, interface gives an R=0.03, or a 3% reflection. This interface must be traversed twice, leading to a 6% reflected component which does not interrogate the sample. These interface mismatches are multiplicative. The fraction of light successfully entering the tissue then must be considered. In some regions of the spectrum, for instance, under a strong water band, almost all of the transmitted light gets absorbed by the tissue. The result is that this seemingly small reflected light component from the refractive index mismatch can virtually swamp out and obscure the desired signal from the sample.

Finally, it is useful to consider the critical angle effect as light attempts to exit the tissue. Tissue is highly scattering and so a light ray which launches into tissue at normal incidence may exit the tissue at a high angle of incidence. If the coupling lens is not in intimate contact with the tissue, these high angle rays will be lost to total internal reflection. The equation which defines the critical angle, or the point of total internal reflection, is as $$\Theta_c = \sin^{-1}\left(\frac{N}{N'}\right)$$

follows:

When light is propagating through a higher index material like tissue ($N'=1.38$) and approaching an interface with lower refractive index like air ($N=1.0$), a critical angle of total internal reflection occurs. Light approaching such an interface at greater than the critical angle will not propagate into the rarer medium (air), but will totally internally reflect back into the tissue. For the aforementioned tissue/air interface, the critical angle is 46.4. No light steeper than this angle would escape. Intimate, optical contact is therefore essential to efficient light capture from tissue.

As detailed above, each of the prior art apparatus for non-invasively measuring glucose concentration utilize a sensor element. Each sensor element includes an input element and an output element. The optical interface between the input element, output element and the skin surface of the tissue to be analyzed in each apparatus is similar. In each instance, the input light energy is transmitted through air to the surface or potentially through air due to a gap in the contact surface between the input sensor and the skin surface. Likewise, the output sensor receives transmitted or reflected light energy via transmission through air to the output sensor, or potentially through a gap between the sensor element and the skin surface even though attempts are made to place the output sensor in contact with the skin. It is believed that the optical interfaces disclosed in the prior art affect the accuracy and consistency of the data acquired utilizing the prior art methods and apparatus. Thus, the accuracy of these methods for non-invasively measuring glucose are compromised.

Wu et al. (U.S. Pat. No. 5,452,723) disclose a method of spectrographic analysis of a tissue sample, which includes measuring the diffuse reflectance spectrum, as well as a second selected spectrum, such as fluorescence, and adjusting the spectrum with the reflectance spectrum. Wu et al. assert that this procedure reduces the sample-to-sample variability. Wu et al. disclose the use of an optical fiber as an input device that is bent at an acute angle so that incident light from the fiber impinges on an optically smooth surface of an optical coupling medium. The optical coupling medium is indexed matched to the tissue so that little or no specular reflection occurs at the interface between the catheter and the tissue. Wu et al. further disclose that the catheter can be used in contact or non-contact modes with the tissue. In contact mode, the end of the catheter is placed in direct contact with the tissue to accomplish index matched optical coupling. Thus, the optical coupling medium of Wu et al. is a solid end portion on the optical fiber. Wu et al. further disclose that the catheter can be used in a non-contact mode, wherein the gap left between the end of the catheter and the tissue can be filled with an index-matched fluid to prevent specular reflections. The only criteria disclosed throughout the Wu et al. specification for the fluid is that it is index matched to prevent specular reflections, which is only one aspect of an optimum optical interface for spectrographic analysis of an analyte in blood.

Accordingly, the need exists for a method and apparatus for non-invasively measuring glucose concentrations in blood which incorporates an improved optical interface. The optical interface should produce consistent repeatable results so that the analyte concentration can be accurately calculated from a model such as that disclosed by Robinson et al. The optical interface should maximize both the input and output light energy from the source into the tissue and from the tissue back to the output sensor. The detrimental effects of gaps due to irregularities in the surface of the skin or the presence of other contaminants should be reduced or eliminated. Means should also be provided to guarantee that such optimized interface is achieved each time a user is coupled to the device for analysis.

The present invention addresses these needs as well as other problems associated with existing methods for non-invasively measuring glucose concentration in blood utilizing infrared spectroscopy and the optical interface associated therewith. The present invention also offers further advantages over the prior art and solves problems associated therewith.

SUMMARY OF THE INVENTION

The present invention is a method for non-invasively measuring the concentration of an analyte, particularly glucose in human tissue. The method utilizes spectroscopic techniques in conjunction with an improved optical interface between a sensor probe and a skin surface or tissue surface of the body containing the tissue to be analyzed.

The method for non-invasively measuring the concentration of glucose in blood includes first providing an apparatus for measuring infrared absorption by an analyte containing tissue. The apparatus includes generally three elements, an energy source, a sensor element, and a spectrum analyzer. The sensor element includes an input element and an output element. The input element is operatively connected to the energy source by a first means for transmitting infrared energy. The output element is operatively connected to the spectrum analyzer by a second means for transmitting infrared energy.

In preferred embodiments, the input element and output element comprise lens systems which focus the infrared light energy to and from the sample. In a preferred embodiment, the input element and output element comprise a single lens system which is utilized for both input of infrared light energy from the energy source and output of both specular and diffusely reflected light energy from the analyte-containing sample.

Alternatively, the input element and output element can comprise two lens systems, placed on opposing sides of an analyte-containing sample, wherein light energy from the energy source is transmitted to the input element and light energy transmitted through the analyte-containing sample then passes through the output element to the spectrum analyzer.

The first means for transmitting infrared energy, in preferred embodiments, simply includes placing the infrared energy source proximate to the input element so that light energy from the source is transmitted via the air to the input element. Further, in preferred embodiments, the second means for transmitting infrared energy preferably includes a single mirror or system of mirrors which direct the light energy exiting the output element through the air to the spectrum analyzer.

In practicing the method of the present invention, an analyte containing tissue area is selected as the point of analysis. This area can include the skin surface on the finger, earlobe, forearm or any other skin surface. Preferably, the analyte-containing tissue in the area for sampling includes blood vessels near the surface and a relatively smooth, uncalloused skin surface. A preferred sample location is the underside of the forearm.

A quantity of an index-matching medium or fluid is then placed on the skin area to be analyzed. The index-matching fluid detailed herein is selected to optimize introduction of light into the tissue, reduce specular light and effectively get light out of the tissue. The medium or fluid preferably contains an additive which confirm proper coupling to the skin surface by a proper fluid, thus assuring the integrity of test data. It is preferred that the index-matching medium is non-toxic and has a spectral signature in the near infrared region which is minimal, and is thus minimally absorbing of light energy having wavelengths relevant to the analyte being measured. In preferred embodiments, the index-matching medium has a refractive index of about 1.38. Further, the refractive index of the medium should be constant throughout the composition. The composition of the index-matching medium is detailed below.

The sensor element, which includes the input element and the output element, is then placed in contact with the index-matching medium. Alternatively, the index-matching medium can be first placed on the sensor element, followed by placing the sensor element in contact with the skin with the index-matching medium disposed therebetween. In this way, the input element and output element are coupled to the analyte containing tissue or skin surface via the index-matching medium which eliminates the need for the light energy to propagate through air or pockets of air due to irregularities in the skin surface.

In analyzing for the concentration of glucose in the analyte containing tissue, light energy from the energy source is transmitted via the first means for transmitting infrared energy into the input element. The light energy is transmitted from the input element through the index-matching medium to the skin surface. Some of the light energy contacting the analyte-containing sample is differentially absorbed by the various components and analytes contained therein at various depths within the sample. Some of the light energy is also transmitted through the sample. However, a quantity of light energy is reflected back to the output element. In a preferred embodiment, the non-absorbed or non-transmitted light energy is reflected back to the output element upon propagating through the index-matching medium. This reflected light energy includes both diffusely reflected light energy and specularly reflected light energy. Specularly reflected light energy is that which reflects from the surface of the sample and contains little or no analyte information, while diffusely reflected light energy is that which reflects from deeper within the sample, wherein the analytes are present.

In preferred embodiments, the specularly reflected light energy is separated from the diffusely reflected light energy. The non-absorbed diffusely reflected light energy is then transmitted via the second means for transmitting infrared energy to the spectrum analyzer. As detailed below, the spectrum analyzer preferably utilizes a computer to generate a prediction result utilizing the measured intensities, a calibration model, and a multivariate algorithm.

A preferred device for separating the specularly reflected light from the diffusely reflected light is a specular control device as disclosed in co-pending and commonly assigned application Ser. No. 08/513,094, filed on Aug. 9, 1995, and entitled "Improved Diffuse Reflectance Monitoring Apparatus", now U.S. Pat. No. 5,636,633, issued Jun. 10, 1997. The above patent disclosure is hereby incorporated by reference.

In an alternative embodiment, the input element is placed in contact with a first quantity of index-matching medium on a first skin surface, while the output element is placed in contact with a second quantity of index-matching medium on an opposing skin surface. Alternatively, the index-matching medium can be placed on the input and output elements prior to skin contact so that the medium is disposed between the elements and the skin surface during measurement. With this alternative embodiment, the light energy propagated through the input element and first quantity of index-matching medium is differentially absorbed by the analyte containing tissue or reflected therefrom, while a quantity of the light energy at various wavelengths is transmitted through the analyte containing tissue to the opposing or second skin surface. From the second skin surface, the non-absorbed light energy is propagated through the second quantity of index-matching medium to the output element with subsequent propagation to the spectrum analyzer for calculation of the analyte concentration.

The index-matching medium of the present invention is a key to the improved accuracy and repeatability of the method described above. The index-matching medium is preferably a composition containing chlorofluorocarbons. The composition can also contain perfluorocarbons. One preferred index-matching medium is a fluoronated-chloronated hydrocarbon polymer oil manufactured by Oxidant Chemical under the tradename FLUOROLUBE.

It has been found that the index-matching mediums of the present invention optimize the analysis of a blood analyte in human tissue by effectively introducing light into the tissue, reducing specular light, and effectively getting light back out of the tissue, which has been diffusely reflected from analyte-containing areas of the tissue, back to the output device. This requires selection of an index-matching medium that not only has the proper refractive index, but also has minimal absorption of infrared energy at wavelengths which are relevant to the measurement of the analyte of interest. Therefore, a preferred index-matching medium of the present invention is minimally or essentially non absorbing of light energy in the near infrared range of the spectrum.

In preferred embodiments, the index-matching medium of the present invention also includes a diagnostic additive. The diagnostic additive in the index-matching fluid allows a determination of the height of the fluid layer and/or provides a wavelength calibration for the instrument. These additives allow for assessment of the quality of the lens/tissue interface and assessment of instrument performance each time an individual is tested utilizing the apparatus of the present invention. The diagnostic additive can account for about 0.2% to about 20% by weight of the overall fluid. In an alternative embodiment, the index-matching medium and the diagnostic additive can comprise the same compound which serves both functions.

The index-matching medium of the present invention can also include physiological additives which enhance or alter the physiology of the tissue to be analyzed. In particular, preferred physiological additives include vasodilating agents which decrease the equilibration time between capillary blood glucose concentration and skin interstitial fluid glucose concentrations to provide a more accurate blood glucose number. The physiological additives can account for about 0.2% to about 20% by weight of the overall fluid.

The compound can also contain other additives such as a hydrophilic additive like isopropyl alcohol. The hydrophilic compound is believed to tie up the moisture in the skin surface to improve the interface between the fluid and skin. Further, the index-matching medium can contain cleansing agents to bind the oil in the skin at the sample point and reduce the effect thereof. Finally, a surfactant can also be included in the fluid composition. The surfactant improves the wetting of the tissue, creating a uniform interface. An antiseptic material can also be added to the index-matching medium.

In an alternative embodiment of the current invention, the index matching between the optical sensor elements and the tissue can be performed by a deformable solid. The deformable solid can alter its shape such that air gaps, due in part to the uneven surfaces of the skin, are minimized. Deformable solids can include at least gelatin, adhesive tape, and substances that are liquid upon application but become solid over time.

The index-matching medium preferably has a refractive index of between 1.30–1.45, more preferably between 1.35–1.40. Utilization of a refractive index in this range has been found to improve the repeatability and accuracy of the above method by improving optical throughput and decreasing spectroscopic variations unrelated to analyte concentration. Further, the index-matching medium should have a consistent refractive index throughout the composition. For example, no air bubbles should be present which cause changes in light direction.

In a preferred embodiment, the concentration of glucose in the tissue is determined by first measuring the light intensity received by the output sensor. These measured intensities in combination with a calibration model are utilized by a multivariate algorithm to predict the glucose concentration in the tissue. The calibration model empirically relates the known glucose concentrations in a set of calibration samples to the measured intensity variations obtained from said calibration samples. In a preferred embodiment, the multivariate algorithm used is the partial least squares method, although other multivariate techniques can be employed.

The use of an index-matching medium to couple the optical sensor's input element and output element to the skin surface reduces the likelihood that aberrant data will be acquired. The index-matching medium increases the repeatability and accuracy of the measuring procedure. Adverse effects on the input and output light energy by transmission through air or uneven surfaces of the skin having pockets of air are eliminated.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

Figure 1:
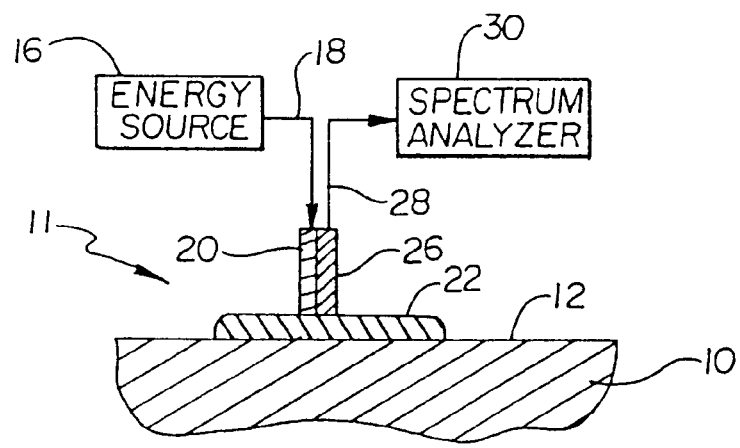
FIG. 1 is a partial cross-sectional view of a sensor element coupled to the skin surface via an indexing-matching fluid.

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is directed to a method for non-invasive measurement of tissue constituents using spectroscopy. It has been found that the sample is a complex matrix of materials with differing refractive indices and absorption properties. Further, because the blood constituents of interest are present at very low concentrations, it has been found to be imperative to couple light into and out from the tissue in an efficient manner. The method of the present invention incorporates an index-matching medium, fluid or deformable solid, to improve the efficiency of coupling the light both into and out of the tissue sample.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. Less than 0.1 percent of the absorption of light is from, for instance, a constituent such as glucose. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index discontinuities are frequent, they are also typically small in magnitude and the scatter generally has a strong directionality towards the forward direction.

This forward scatter has been described in terms of anisotropy, which is defined as the cosine of the average scatter angle. Thus, for complete backwards scatter, meaning that all scatter events would cause a photon to divert its direction of travel by 180 degrees, the anisotropy factor is −1. Likewise, for complete forward scatter, the anisotropy factor is +1. In the near infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In analyzing for an analyte in tissue, measurements can be made in at least two different modes. It is recognized that one can measure light transmitted through a section of tissue, or one may measure light reflected or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wave lengths. Thus, the preferred method for measurement in the present invention is to focus on the reflectance of light from the sample.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possess an outward layer which is essentially dead and lacks concentration values of the analytes generally considered of interest in a sample. Thus, reflected light energy containing analyte information is that light which is reflected back to the surface through refractive index discontinuities deeper within the tissue sample. This reflected light energy is referred to as diffusely reflected light.

Applicants have found that a large fraction of incident photons are absorbed in the tissue. Those photons which are available for coupling back out of the tissue are likely diverted in their angular path. In fact, by definition, a photon must change direction in order to exit the tissue in a direction towards the input optic. Applicants, however, have found that a large problem associated with detection is associated with the refractive index discontinuity between the average tissue refractive index and the refractive index of air outside of the tissue. It has been found that this discontinuity acting on incident light leads to a refraction and a small specular reflectance of less than about 5 percent. However, on the way out, the discontinuity gives rise to a critical angle phenomenon. Because the photon is traveling from a high refractive index medium to a lower one, a critical angle exists above which a photon is totally internally reflected and will not escape the tissue sample. This critical angle for photons traveling from tissue to air has been found to be about 46 degrees, which presents a problem. A photon normally incident on the tissue surface must deviate through a large angle to exit. Because of the forward directionality of scattering, this is difficult for a photon to do, and it is very likely to make a grazing or high angle incidence with the tissue and air interface. The grazing incidence photons will not escape because the critical angle is exceeded.

Applicants have found a solution for the differences in refractive index associated with coupling light energy exiting tissue to an analytical instrument. The solution is the use of an immersion fluid which has very low absorptivity in the spectral range of interest, and has a viscosity compatible with good flow and coverage, while having a refractive index which closely matches tissue. In preferred embodiments, the index matching fluid is preferably minimally or essentially non-absorbing of light energy in the wavelengths relevant to the blood analyte under study. The fluid is thus non-spectroscopically active at desired wavelengths. However, it is believed a minimally absorbing index-matching fluid, for example one that absorbs less than about 10% of the light energy of analyte relevant wavelengths, could still be utilized. A preferred material is a fluorinated, chlorinated hydrocarbon polymer oil manufactured by Occidental Chemical under the tradename FLUOROLUBE. FS5 is a preferred FLUOROLUBE. These oils have a refractive index of about 1.38, are non-toxic, and Applicants have found that it has a spectral signature in the near infrared region which is minimal.

Figure 2:
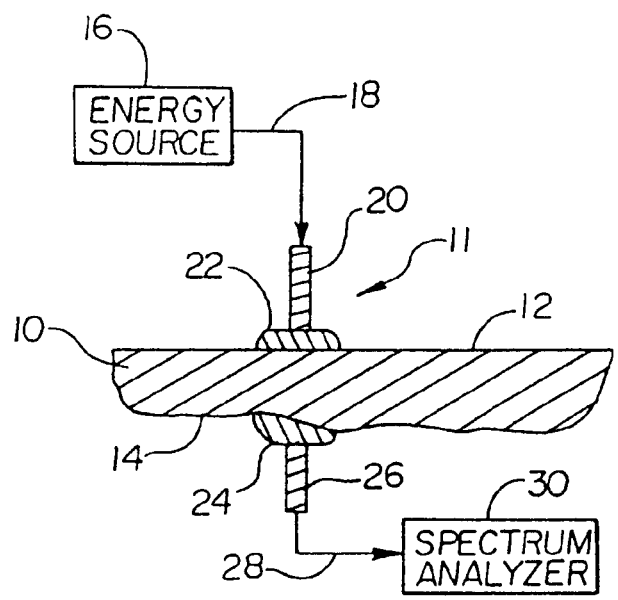
FIG. 2 is a partial cross-sectional view of an alternative embodiment of a sensor element coupled to opposite sides of a skin surface via an indexing-matching fluid.

Now referring to FIGS. 1 and 2, partial cross-sectional views of two preferred embodiments of an apparatus for non-invasively measuring a blood analyte concentration are depicted. The depictions in FIGS. 1 and 2 are schematic to depict the concept of utilizing an index-matching medium 22 in conjunction with a non-invasive sensor element 11 operatively connected to an energy source 16 and a spectrum analyzer 30. The relative size, shape and detail of physical components are not depicted. The apparatus depicted in FIG. 1 and the apparatus depicted in FIG. 2 generally include three elements, an energy source 16, a sensor element 11, and a spectrum analyzer 30. The embodiment of FIG. 1 depicts the sensor element as including an input element 20 and an output element 26, which can include a single lens system for both input and output light energy. The input element 20 and output element 26 are in contact with a common skin surface 12 of an analyte-containing tissue 10. The alternative embodiment of FIG. 2 depicts an alternative sensor element 11 arrangement, wherein the input element 20 and output element 26 are arranged on opposing surfaces 12, 14 of an analyte containing tissue 10. Both embodiments function to give a measure of the absorption of infrared energy by the analyte-containing tissue 10. However, the embodiment of FIG. 1 is utilized to measure the quantity of light energy which is reflected from the analyte-containing tissue 10 by the analyte components therein. In contrast, the embodiment of FIG. 2 measures the transmission of light energy through the analyte-containing tissue 10. In either embodiment, the absorption at various wavelengths can be determined by comparison to the intensity of the light energy from the energy source 16.

The energy source 16 is preferably a wide band, infrared black body source. The optical wavelengths emitted from the energy source 16 are preferably between 1.0 and 2.5 $\mu$m. The energy source 16 is operatively coupled to a first means for transmitting infrared energy 18 from the energy source to the input element 20. In preferred embodiments, this first means 18 is simply the transmission of light energy to the input element 20 through air by placing the energy source 16 proximate the input element 20.

The input element 20 of the sensor element 11 is preferably an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In both embodiments depicted in FIGS. 1 and 2, an output sensor 26 is utilized to receive reflected or transmitted light energy from the analyte containing tissue 10. As described in conjunction with a method of analysis below, the embodiment of FIG. 1 has an output sensor 26 which receives reflected light energy, while the embodiment of FIG. 2 includes an output sensor 26 which receives transmitted light through the analyte-containing tissue 10. As with the input element 20, the output element 26 is preferably an optical lens. Other optical collection means may be incorporated into an output element 26, such as a multiple lens system, tapered fiber, or other beam-collection means to assist in directing the light energy to the spectrum analyzer 30.

A second means for transmitting infrared energy 28 is operatively connected to the output element 26. The light transmitted through the second means for transmitting infrared energy 28 is transmitted to the spectrum analyzer 30. In a preferred embodiment, the operative connection to the output element includes transmission of the reflected or transmitted light energy exiting the output element through air to the spectrum analyzer 30. A mirror or series of mirrors may be utilized to direct this light energy to the spectrum analyzer. In a preferred embodiment, a specular control device is incorporated to separate the specular reflected light from diffusely reflected light. This device is disclosed in co-pending and commonly assigned application Ser. No. 08/513,094, filed Aug. 9, 1995, and entitled "Improved Diffuse Reflectance Monitoring Apparatus", now U.S. Pat. No. 5,636,633, issued Jun. 10, 1997, the disclosure of which is incorporated herein by reference.

In practicing the method of the present invention, an analyte-containing tissue 10 area is selected as the point of analysis. This area can include the skin surface 12 on the finger, earlobe, forearm, or any other skin surface. Preferably, the area for sampling includes blood vessels near the surface, and a relatively smooth, uncalloused surface. A preferred sample location is the underside of the forearm.

A quantity of an index-matching medium 22, whether fluid or deformable solid, is then placed on the skin surface 12 in the area to be analyzed. The sensor element 11, which includes the input element 20 and the output element 26, as depicted in the embodiment of FIG. 1, is then placed in contact with the index-matching medium 22. Alternatively, a quantity of index-matching medium 22 can be placed on the sensor element 11, which is then placed in contact with the skin surface 12 with the index-matching medium 22 disposed therebetween. In either procedure, the input element 20 and output element 26 are coupled to the analyte-containing tissue 10 or skin surface 12 via the index-matching medium 22. The coupling of the sensor element 11 with the skin surface via the index-matching medium 22 eliminates the need for light energy to propagate through air or pockets of air due to a space between the probe and the skin surface 12 or irregularities in the skin surface 12.

In analyzing for the concentration of glucose in the analyte-containing tissue 10, light energy from the energy source 16 is transmitted through the first means for transmitting infrared energy 18 into the input element 20. The light energy is transmitted from the input element 20 through the index-matching medium 22, to the skin surface 12. The light energy contacting the skin surface 12 is differentially absorbed by the various components and analytes contained below the skin surface 12 with the body (i.e., blood within vessels) therein. In a preferred embodiment, the non-absorbed light energy is reflected back to the output element 26 upon propagating again through the index-matching medium 22. The non-absorbed light energy is transmitted via the second means for transmitting infrared energy 28 to the spectrum analyzer 30.

In the alternative embodiment of FIG. 2, the input element 20 is placed in contact with a first quantity of index-matching medium 22 on a first skin surface 12, while the output element 26 is placed in contact with a second quantity of index-matching medium 24 on an opposing skin surface 14. As with the previous embodiment, the index-matching medium 22 can be first placed on the input element 20 and output element 26 prior to contact with the skin surface 12. With this alternative embodiment, the light energy propagated through the input element 20 and first quantity of index-matching medium 22 is differentially absorbed by the analyte-containing tissue 10, while a quantity of the light energy at various wavelengths is transmitted through the analyte-containing tissue 10 to the opposing or second skin surface 14. From the second skin surface 14, the non-absorbed light energy is propagated through the second quantity of index-matching medium 24 to the output element 26 with subsequent propagation to the spectrum analyzer 30 for calculation of the analyte concentration.

As previously stated, the index-matching medium 22 of the present invention is a key to the improved accuracy and repeatability of the method described above. The index-matching medium can preferably be a fluid composition containing chlorofluorocarbons. The composition can also be a mixture of chlorofluorocarbons and perfluorocarbons. A preferred composition includes chlorotrifluoroethylene. A preferred composition contains about 80% to about 99.8% by weight of chlorofluorocarbons. As previously stated, the present invention utilizes an index-matching fluid to optimize the input and output of light energy to and from a sample containing an analyte of interest to be measured. In its broadest sense, the index-matching fluid of the present invention can be any fluid which creates an improved optical interface over that interface which results from simply placing the probe of the present invention on a skin surface. Absent the index-matching fluid of the present invention, this interface can include gaps which are air filled and cause detrimental refraction of light both going into the tissue and exiting the tissue. Thus, any index-matching fluid having a refractive index closer to that of the tissue at about 1.38 versus the refractive index of air of about 1.0 would provide an improved interface.

Applicants have also recognized that the usefulness of the apparatus of the present invention requires that the coupling of the sensor be repeatable and that the results be an accurate reflection of the blood glucose level of the patient. To this end, Applicants have found that it is preferable for the index-matching fluids of the present invention to contain diagnostic additives and/or physiological additives. The diagnostic additives provide an assessment of the quality of the lens to tissue interface and/or an assessment of the instrument's present performance, while the physiological additives alter the physiology of the tissue to correct for differences in tissue analyte concentration versus blood analyte concentration. A discussion of these additives follows.

The non-invasive measurement of glucose in tissue by the present invention is improved by placing an additive into the index-matching fluid that allows evaluation of the thickness of the fluid when the tissue is placed in contact with the instrument. In preferred embodiments, the additive also provides a calibration of the instrument by including a compound of known high absorption at a specified wavelength of light. Such additives also further assure that the correct index-matching fluid is being utilized for the instrument.

Since an index-matching fluid inherently causes a change of height in the tissue above the sample probe, the measurement of this height can aid in the overall glucose or other analyte measurement, while allowing a path length correction to be applied to the spectral measurement as a function of the tissue height above the sampler. This can insure a reproducible, consistent height is achieved before commencing the spectral measurement of the tissue, and further allows for the adjustment of the height before commencing the spectral measurement of the tissue. In this way, the user can be certain that spurious results are not achieved due to excess matching fluid height, insufficient index-matching fluid being utilized, or some other misplacement of the tissue surface relative to the analyzer.

Laboratory spectrometers utilize a Fourier Transform system which incorporates a laser reference signal to establish the wavelengths and guarantees that the instrument is calibrated. However, it is likely instruments that are affordable for an end user will not use a laser, but rather will be dispersion type instruments such as gratings, CCD arrays and others. With such instruments, it is important to make certain that calibration is proper prior to each analysis of blood analyte. To this end, Applicants have found that the addition of an additive which includes a well-defined spectral feature at a known wavelength of light can be utilized to assure calibration.

The use of a known spectrally active additive to the index-matching fluid also insures that the end user is using a correct index-matching fluid for which the instrument has been calibrated and programmed. The use of a different index-matching fluid could result in an error in the non-invasive analyte measurement by absorbing light energy in the areas of interest for the particular analyte.

To accomplish the above repeatability, accuracy and quality assurance, a spectroscopically active agent is preferably added to the index-matching fluid. The agent preferably has sharp bands of absorption outside the region of interest to measure the blood analyte. For example, in a preferred method for glucose analysis, the agent would be active outside the ranges of 4200–4900 and 5400–7200 wave numbers. The agent could also be active within this range so long as there is no significant overlap with wavelengths actually used to calculate glucose concentration. The additive can be manufactured by placing an appropriate functional group on perfluorinated hydrocarbons. The perfluorinated hydrocarbons are spectrally inactive in the region of interest, however, the functional group placed upon the perfluorinated hydrocarbons may be spectrally active. Further, these functional groups do not interfere with the analysis of the blood analyte of interest. Exemplary compounds include perfluoro-2-butyltetrahydrofuran and perfluorosuccinyl chloride.

In an alternative embodiment, the index-matching fluid and diagnostic additive can comprise the same fluid which provides both functions. For example, perfluoro-2-butyltetrahydrofuran can be utilized as an index-matching medium which improves the optical interface, and at the same time includes a functional group which makes the compound spectrographically active in a desired range for diagnostic purposes.

The near infrared light energy of the present invention is preferably utilized to measure a blood analyte such as glucose. However, the light energy interrogates the skin as a whole, while the blood vessels make up less than 10% of the skin volume. Therefore, in reality the total skin glucose content is being used as a surrogate for blood glucose concentration. This fact can lead to inaccurate test results if there is a large difference between the tissue glucose concentration and the blood vessel glucose concentration, such as in times of rapidly rising or falling blood glucose levels. Blood glucose can rise acutely after a meal or during glucose production by the liver, while there is a commensurate but lagged rise of the skin glucose concentration. This lag, due to the finite time required for the glucose to diffuse into the greater skin water compartment, can take minutes to tens of minutes depending upon the magnitude of the rise and the surface area of the capillaries available for diffusion. Applicants have found that by increasing the superficial skin capillary blood flow in the area of analysis, the surface area of the capillaries increases and the rate of diffusion of glucose from the vessels into the skin also increases significantly. This markedly results in reduced equilibration times and a significant reduction in measurement error attributable to the disequilibrium between blood glucose and skin water glucose concentration during periods of changing blood glucose concentration.

Applicants have found that vasodilating agents which are topically applied can provide the improved equilibration. These agents work by diffusing into the skin and blocking the adrenergic receptors on the small arterioles that feed the capillary vessels. This results in dilation of the arterial sphincters, a reduction of resistance to flow, and an increase in pressure and size of the capillaries. A number of preferred vasodilating agents include: methyl nicotinamide, minoxidil, nitroglycerin, histamine, menthol, and capsaicin.

The compound can contain a hydrophilic additive, such as isopropyl alcohol. The hydrophilic additive is believed to tie up the moisture in the skin surface to improve the interface between the medium and the skin. Further, the index-matching medium can contain cleansing agents to bind the oil in the skin at the sample point and reduce the effect thereof. A surfactant can also be included in the composition. The surfactant improves the wetting of the tissue, thus improving contact. Finally, an antiseptic compound can be added to the index-matching medium.

In an alternative embodiment of the current invention, the index matching between the optical sensor elements and the tissue can be performed by a deformable solid. The deformable solid can alter its shape such that air gaps, due in part to the uneven surfaces of the skin, are minimized. Deformable solids can include at least gelatin, adhesive tape, and substances that are liquid upon application but become solid over time.

The index-matching medium, preferably has a refractive index of 1.30–1.45, more preferably from 1.35–1.40. Utilization of a refractive index in this range has been found to improve the repeatability and accuracy of the above method. It is recognized that the refractive index of the index-matching medium must be consistent throughout the composition to prevent refraction of light energy as it passes through the medium. For example, there should be no air bubbles present in the index-matching medium which could cause a discontinuity in refractive index.

In a preferred embodiment, the concentration of glucose in the tissue is determined by first measuring the light intensity received by the output sensor. These measured intensities in combination with a calibration model are utilized by a multivariate algorithm to predict the glucose concentration in the tissue. The calibration model empirically relates the known glucose concentrations in the calibration samples to the measured intensity variations obtained from said calibration samples. In a preferred embodiment, the multivariate algorithm used is the partial least squares method, although other multivariate techniques can be employed.

The input infrared energy from the input element sensor is coupled to the analyte-containing sample or blood through the index-matching medium 22. There is, thus, differing absorption at several wavelengths of the infrared energy as a function of the composition of the sample. The differing absorption causes intensity variations of the infrared energy passing through the analyte containing samples. The derived intensity variations of the infrared energy are received by reflectance or transmittance through the analyte-containing sample by the output element of the sensor, which is also coupled to the blood or analyte-containing sample through the index-matching medium 22.

The spectrum analyzer 30 of the present invention preferably includes a frequency dispersion device and photodiode array detectors in conjunction with a computer to compare the data received from such devices to the model discussed above. Although preferable, other methods of analyzing the output energy may be utilized.

The frequency dispersion device and photodiode array detectors are arranged so that the array includes multiple output leads, one of which is assigned to a particular wavelength or narrow range of wavelengths of the energy source 16. The amplitude of the voltage developed on each of the leads is commensurate with the intensity of the infrared energy incident on each particular detector in the array for the wavelength of the source associated with that detector. Typically, the photodiodes of the array detector are passive, rather than photovoltaic, although photovoltaic devices may be employed. The diodes of the array detector must be supplied with DC power supply voltage as derived from a power supply and coupled to the diodes of the array detector via a cable. The impedance of the diode elements of the array detector are changed as a function of the intensity of the optical energy incident thereon in the pass band of the energy source 16 associated with each particular photodiode element. The impedance changes can control the amplitude of the signal supplied by the array detector to a random access memory computer.

The computer includes a memory having stored therein a multivariate calibration model empirically relating the known glucose concentration in a set of calibration samples to the measure intensity variations from said calibration samples, at several wavelengths. Such a model is constructed using techniques known by statisticians.

The computer predicts the analyte concentration of the analyte-containing sample 10 by utilizing the measured intensity variations, calibration model and a multivariate algorithm. Preferably, the computation is made by the partial least squares technique as disclosed by Robinson et al. in U.S. Pat. No. 4,975,581, incorporated herein by reference.

It is has been found that considerable improvement in detection precision is obtained by simultaneously utilizing at least several wavelengths from the entire spectral frequency range of the energy source 16 to derive data for a multivariate analysis. The multivariate method allows both detection and compensation for interferences, the detection of meaningless results, as well as for modeling many types of non-linearities. Since the calibration samples used to derive the models have been analyzed on a multivariate basis, the presence of unknown biological materials in the analyte containing tissue 10 does not prevent or distort the analysis. This is because these unknown biological materials are present in the calibration samples used to form the model.

The partial least squares algorithm, calibration model and measured intensity variations are employed by the computer to determine the concentration of the analyte in the analyte containing tissue 10. The indication derived by the computer is coupled to conventional alphanumeric visual displays.

Experimental

Figure 3:
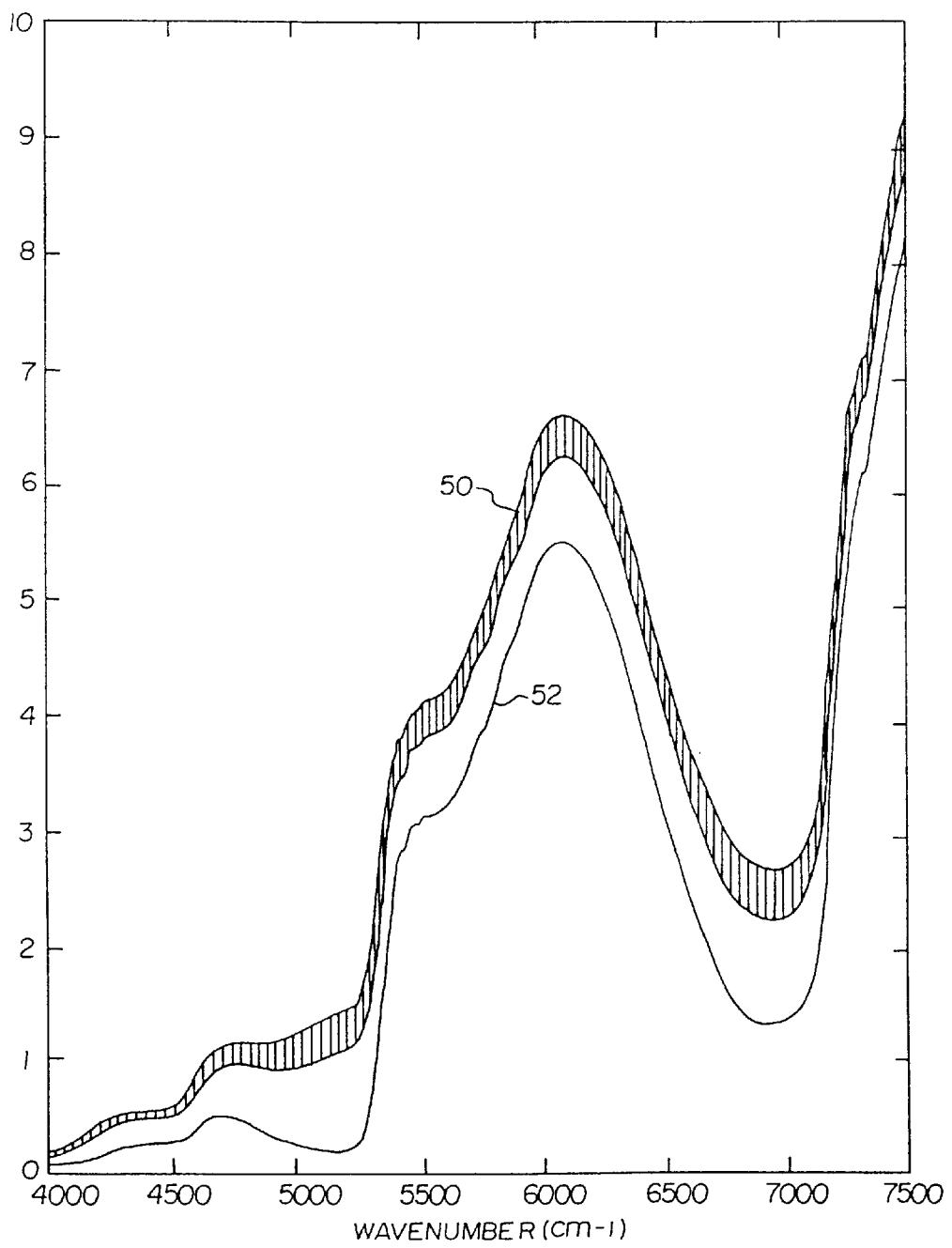
FIG. 3 is a graphical representation of experimental data showing the improvement in accuracy and repeatability of a sensor coupled to the skin via an index-matching medium.

Comparative testing was conducted to document the effect of utilizing an index-matching medium versus no index-matching medium on the same apparatus. Reference should be made to FIG. 3 which is a graphical representation of the results of the experiment, wherein line 50 represents analysis without the index-matching medium, and line 52 documents the improved accuracy of the result when the sensor element is coupled to the skin surface via an index-matching medium. To conduct the test, forearm sampling was conducted with and without the index-matching medium with a two minute time resolved data collection.

The apparatus utilized to conduct the experiment included a Perkin-Elmer (Norwalk, CT) System 2000 Fourier Transform Infrared Spectrometer (FTIR) with a 4 mm DIA indium antimonide (InSb) single element detector. The light source was a 100 watt quartz tungsten halogen light bulb from Gilway Technical Lamp (Woburn, Mass.). The interferometer employed an infrared transmitting quartz beamsplitter. Data collection was via a transputer link to a PC running Perkin-Elmer TR-IR software. Data visualization was accomplished in Matlab (MathWorks, Natick, Mass.). Sampling optics were constructed in-house and consisted, in part, of the optical system described in co-pending application 08/513,094, filed Aug. 9, 1995, entitled "Improved Diffuse Reflectance Monitoring Apparatus", now U.S. Pat. No. 5,636,633, issued Jun. 10, 1997. All instrument parameters were identical for the collection of both spectra.

The experimental procedure was as follows. The sampling surface consisted of a $MgF_2$ hemisphere mounted with its radiused side facing downward, and its flat surface placed horizontally. Light was launched into the hemisphere from below. The flat surface of the hemisphere, the mount for the hemisphere, and the holder for the mount all comprised a flush, horizontal sampling surface. The patient's arm was placed down on this surface, such that the underside of the forearm rested against the hemisphere sampling surface. The forearm area had previously been shaved and washed with soap and water, then swabbed with isopropyl alcohol. The arm was then covered with a blood pressure cuff which was inflated to a pressure of 30 mm Hg. The cuff acted to hold the arm in place and to prevent motion of the arm relative to the hemisphere. The sampling surface was held at a constant temperature of 28 C. by resistance heater elements and a thermocouple feedback device. After the arm was situated in the device, it was allowed to equilibrate for 30 seconds prior to sampling.

Referring to FIG. 3, the top trace, labeled 50, shows the result obtained when sampling in the previously described mode in the absence of index-matching medium. In the bottom trace, labeled 52, 100 microliters of chlorotrifluoroethene was applied to the surface of the hemisphere prior to placing the arm. There are several notable differences. Most apparent is the spread of the data. 50 and 52 are each comprised of multiple spectra. With FLUOROLUBE, all of the spectra overlay each other quite closely. This indicates that the interface is quite stable. Without FLUOROLUBE, the interface is extremely unstable. Also, notable is the data near 5200 $cm^{-1}$. This is the position of the strongest water band. Without FLUOROLUBE, this band appears weaker, since it is contaminated with specular light. In fact, note that the spread of the data is largest under this band. In fact, the difference between the two traces can be attributed largely to spurious energy from specular contamination.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A method for evaluating the separation of a sensor element for spectrographic analysis relative to tissue under analysis comprising the steps of:
    providing an apparatus for spectrographic analysis, said apparatus including an energy source emitting energy at multiple wavelengths, including selected wavelengths relevant to measuring an attribute of interest in said tissue, an input element, an output element, and a spectrum analyzer;
    providing a medium, said medium having a known spectral absorbance, and disposing a quantity of said medium between said tissue and said input element and output element to couple said elements to said tissue through said medium;

irradiating said tissue through said input element with said multiple wavelengths of energy; and collecting at least a portion of said energy with said output element and evaluating the separation of the sensor element based on the spectral absorbance of the medium.

2. The method of claim 1, wherein evaluating the separation of the sensor element based on the spectral absorbance of the medium comprises evaluating the distance between the tissue and the sensor element.

3. The method of claim 1, further comprising the step of deriving a pathlength correction for the analysis based on the evaluated separation of the sensor element.

4. The method of claim 1, wherein said medium is a fluid composition comprising about 0.2% to about 20% of a compound having a known spectral absorbance.

5. The method of claim 1, further comprising the step of determining the attribute of the interest only when proper coupling is confirmed.

6. A method for evaluating instrument calibration during non-invasive determination of an attribute of tissue comprising the steps of:

providing an apparatus for spectrographic analysis of tissue, said apparatus including an energy source emitting energy at multiple wavelengths, including selected wavelengths relevant to said attribute of tissue, an input element, said apparatus further including an output element and a spectrum analyzer;

providing a medium, said medium having known spectral absorbance, and disposing a quantity of said medium between said tissue and said input element and output element to couple said elements to said tissue through said medium;

irradiating said tissue through said input element; and collecting at least a portion of the energy with said output element and evaluating instrument calibration utilizing the spectral absorbance of said medium.

7. The method of claim 6, further comprising the step of determining said attribute of tissue only after instrument calibration is confirmed.

8. The method of claim 6, wherein said medium is a fluid composition comprising about 0.2% to about 20% of a compound having said spectral absorbance.

9. The method of claim 6, wherein substantially all of said medium comprises a compound having said known spectral absorbance.

* * * * *